(12) United States Patent
Blake et al.

(10) Patent No.: US 7,829,555 B1
(45) Date of Patent: Nov. 9, 2010

(54) DRUG TARGETING

(75) Inventors: David Blake, Aylesbury (GB); Declan Naughton, Badminton (GB); Ged Adams, Wheatley (GB); Margaret Adams, legal representative, Holton (GB); Ian Stratford, Hope Valley (GB); Christopher Morris, Chippenham (GB); Mohammed Jaffar, Withington (GB); Matthew Naylor, West Cheshunt (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 09/367,261

(22) PCT Filed: Feb. 13, 1998

(86) PCT No.: PCT/GB98/00461

§ 371 (c)(1),
(2), (4) Date: Aug. 10, 2001

(87) PCT Pub. No.: WO98/35701

PCT Pub. Date: Aug. 20, 1998

(30) Foreign Application Priority Data

Feb. 13, 1997 (GB) ............................... 9703002.7
Jun. 10, 1997 (GB) ............................... 9712090.1

(51) Int. Cl.
*A61K 31/573* (2006.01)
*C07J 5/00* (2006.01)

(52) U.S. Cl. ................ 514/179; 514/681; 514/690; 552/297; 552/299; 552/307; 552/581

(58) Field of Classification Search ............. 549/469; 514/412, 179, 681, 690; 552/297, 299, 307, 552/581
See application file for complete search history.

(56) References Cited

U.S. PATENT DOCUMENTS

| 5,086,068 | A | 2/1992 | Raleigh et al. |
| 5,387,692 | A | 2/1995 | Riley et al. |
| 5,652,255 | A | 7/1997 | Adams et al. |

FOREIGN PATENT DOCUMENTS

| GB | 2 131 020 | 6/1984 |
| WO | WO 93/00900 | 1/1993 |
| WO | WO 93/00904 | 1/1993 |
| WO | WO 93/05054 | 3/1993 |
| WO | WO 94/06797 | 3/1994 |
| WO | WO 94/06798 | 3/1994 |
| WO | WO 94/22483 | 10/1994 |
| WO | WO 97/23456 | 7/1997 |

OTHER PUBLICATIONS

Oellinger et al, "Study on the redox properties of naphthazarin (5,8-dihydroxy-1,4-naphthoquinone) and its glutathionyl conjugate in biological reactions: one- and two-electron enzymic reduction", *Chemical Abstracts*, vol. 112, No. 11, Mar. 12, 1990, Columbus, Ohio, US; and *Arch. Biochem. Biophys.* (1989).

Firestone et al, "Nitro heterocycle reduction as a paradigm for intramolecular catalysis of drug delivery to hypoxic cells", *J. Med. Chem*, (1991), 34(9).

Chikhale et al, "Tumor targeted prodrugs: Redox-activation of conformationally constrained, bioreductive melphalan prodrugs", *Eighty-Eighth Annual Meeting of the American Association for Cancer Research*, San Diego, California, USA, Apr. 12-16, 1997. *Proceedings of the American Association for Cancer Research Annual Meeting* (38 (0). 1997. 432-433.

Mehta et al, "Potential bioreductively activated hypoxia probes and post-irradiation radiosensitizers related to NITP", *Anti-Cancer Drug Des.* (1995), 10(3), 227-41.

Hodgkiss et al, "Pharmacokinetics and binding of the bioreductive probe for hypoxia, NITP: effect of route of administration", *Br. J. Cancer*, vol. 72, 1995, pp. 1462-1468.

Berglund, "Bioreductive Heterosubstituted Quinone Antitumor Drug Delivery Agents", *Database Dissabs*, 1987.

Edmonds et al, "Hypoxia and the Rheumatoid Joint: Immunological and Therapeutic Implications", Scand. J. Rheumatol. 24(Suppl 101):163-168 (1995).

Notification of Transmittal of The International Preliminary Examination Report issued in connection with PCT/GB98/00461 dated May 18, 1999.

The Merck Index, "Glutathione", p. 703, item 4369 (1989).

Japanese Official Action.

Ollinger et al, "Study of the Redox Properties of Napthazarin (5,8-Dihydroxy-1,4-naphthoquinone) and its Glutathionyl Conjugate in Biological Reactions: One- and Two-Electron Enzymatic Reduction", Archives of Biochemistry and Biophysics 275(2):514-530 (1989).

Firestone et al, "Nitroheterocycle Reduction as a Paradigm for Intramolecular Catalysis of Drug Delivery to Hypoxi Cells", J. Med. Chem. 34(9):2933-2935 (1991).

Cotterill et al, "Cyclopropamitosenes, Novel Bioreductive Anticancer Agents. Synthesis, Electrochemistry, and Biological Activity of 7-Substituted Cyclopropamitosenes and Related Indolequinones", J. Med. Chem. 37(22):3834-3843 (1994).

*Primary Examiner*—Bernard Dentz
(74) *Attorney, Agent, or Firm*—Nixon & Vanderhye P.C.

(57) ABSTRACT

The invention provides a method of targeting a drug to areas of hypoxic and/or ischemic tissue within the body in which the desired drug species is linked to a non-cytotoxic bioreductive carrier. Also provided by the invention are novel bioreductive conjugates comprising a non-cytotoxic bioreductive moiety with linked-thereto at least one therapeutic agent. The compounds of the invention are particularly suitable for the treatment of rheumatoid arthritis and other arthritic conditions, diabetes, atherosclerosis, stroke, sepsis, Alzheimer's disease and other neurological disorders, cancer, kidney disease, digestive diseases, liver disease, chronic periodontitis or ischemia following tissue transplantation.

8 Claims, 1 Drawing Sheet

FIGURE 1

DRUG TARGETING

This application is the U.S. national phase of International Application No. PCT/GB98/00461, filed Feb. 13, 1998, which designated the U.S. and claims priority from UK Application No. 9703002.7, filed Feb. 13, 1997 and UK Application No. 9712090.1, filed Jun. 10, 1997.

The present invention relates to bioreductive drug conjugates for use in targeting of therapeutic agents to localised regions of hypoxic and/or ischemic tissue within the body.

Reduced oxygen tension (hypoxia) has been demonstrated in a variety of tumor types. In fact, it has long been suspected that oxygen deficiency in tumors may be a limiting factor in the control of tumors by radiotherapy. Relatively recently, the presence of hypoxia in tumors has been exploited in their treatment.

Bioreductive drugs require metabolic reduction to generate cytotoxic metabolites. This process is facilitated by the presence of appropriate reductases and the lower oxygen conditions present in some cancerous (hypoxic) as compared to normal (normoxic) tissue. As a result, a number of bioreductive drugs capable of producing cytotoxic metabolites under hypoxic conditions have been proposed for use in combination with radiotherapy treatment of tumors.

A number of bioreductive compounds are known to act as potent alkylating agents after undergoing reduction in vivo. Examples of known bioreductive alkylating agents include compounds such as activated enamines, vinylogous quinone methides, simple quinone methides and α-methylene lactones or lactams. Bioactivation of such compounds produces species which are electron deficient and which are capable of covalent binding to a nucleophilic centre on a biomolecule, such as DNA.

Most bioreductive drugs that have been developed for use in the treatment of tumors exhibit an optimum "trapping" potential when hypoxia is profound ($pO_2$<12 mm Hg) and this is believed to form the basis for their selectivity for cancerous as opposed to normal tissues.

Bioreductive drugs have also been proposed for use in several methods for the detection of hypoxic cells in tumors. In this way, radiotherapy treatment may be optimised for individual patients on the basis of the oxygen status of their tumors.

U.S. Pat. No. 5,086,068 describes the use of nitroaromatic compounds in the detection of hypoxic cells in normal and tumor tissue. An immunogenic conjugate comprising a nitroaromatic compound and an immune response inducing carrier is used in vitro to raise antibodies specific to the nitroaromatic compound. These antibodies are in turn used to detect the presence of hypoxic tissue following in vivo administration of the nitroaromatic compound.

A number of methods have also been described for detecting the presence of hypoxic cells in tumors using a labelled 2-nitroimidazole in which labelled fragments of the nitroimidazole compound bind to cellular macromolecules. More recently, the use of an immunologically detectable hapten such as theophylline covalently bound to a 2-nitroimidazole has been suggested as a method of identifying hypoxic cells (see Brit. J. Cancer 63: 119-125, 1991 & 72: 1462-1468, 1995, and Anti-Cancer Drug Design 10: 227-241, 1995). Bioreduction of the nitroimidazole leads to binding of bioreductive metabolites, and hence the theophylline side-chain, to intracellular molecules. Immunochemical techniques are then used to stain and thus locate those cells containing the bound theophylline.

Other agents comprising a bioreductive moiety, e.g. 2-nitroimidazole, for the diagnosis or treatment of hypoxic cells are described in U.S. Pat. No. 5,387,692.

A number of bioreductive agents have been described for use in the delivery of cytotoxic drugs to hypoxic tumor tissue in which bioreductive activation at the tumor site results in selective delivery of the drug. However, following drug delivery the bioreductive compound remaining in the tissues is itself a potential alkylating agent and thus cytotoxic, thereby rendering such a system entirely unsuitable for use as a non-cytotoxic drug delivery vehicle in diseases other than cancer. Hypoxia-selective bioreductive drug delivery agents proposed for use in anti-tumor therapy are described, for example, in Dissabs. 87: 31004, 1987 and in J. Med. Chem. 21: 2933-2935, 1991.

Delivery systems which utilise bioreduction to deliver a non-cytotoxic drug species have also been proposed. For example, a delivery system based on quinone propionic acid has been described (see Pharmaceutical Research 8(3): 323-330, 1991) in which the benzoquinone acts as the trigger and the propionic acid moiety allows for linkage either to an amine moiety (e.g. an enzyme inhibitor) or to an alcohol (e.g. a steroid). Two electron activation of the benzoquinone trigger facilitates intramolecular cyclisation generating a stable lactone, a process which results in elimination of the drug species. However, the lactone produced is itself a potential alkylating agent. This system is thus unsuitable for use as a non-cytotoxic drug delivery system. Furthermore, in aqueous solution in the absence of a reducing agent the lactone produced following drug delivery is very unstable and undergoes degradation. The instability of this prodrug system in aqueous solution thus precludes its use for drug delivery in vivo.

We now propose an improved method for the specific targeting of a drug to areas of hypoxic and/or ischemic tissue, e.g. cells, tissues and/or organs, within the body in which the desired drug species is linked to a non-cytotoxic bioreductive compound or carrier. In this method, any direct interaction of the carrier with DNA or other biomolecules is minimised, thus avoiding potential mutagenic side effects.

In particular, we now propose a method capable of targeting drugs to sites of inflammation within the body associated with hypoxia and/or ischemia, e.g. to the synovium in the treatment of rheumatoid arthritis. This method not only has the effect of reducing the risk of systemic side effects of the drug, but also enhances the therapeutic effect of the drug.

Thus, viewed from one aspect the invention provides a bioreductive conjugate comprising a non-cytotoxic bioreductive moiety with linked thereto at least one therapeutic agent.

The bioreductive conjugates in accordance with the invention are substantially stable in an oxygenated environment. However, in a hypoxic or ischemic environment, reductive activation results in release of the therapeutic agent from the bioreductive moiety and thus its targeted delivery to the site of hypoxia or ischemia which may be an organ, tissue, cell or group of cells. In general, on bioreduction the bioreductive moiety will undergo an intramolecular rearrangement or intramolecular cyclisation reaction which in turn provides for release of the therapeutic agent at the target site.

As used herein, the term "bioreductive moiety" is intended to define any molecule which is reduced in the presence of reducing enzymes or reductases. For example, a bioreductive moiety may be any substantially non-reactive molecule which in the presence of reductases is converted into a more reactive form. Preferred bioreductive moieties for use in the invention are those which on reductive activation become electron-rich and which are thereby capable of intramolecular bond rearrangement to deliver a therapeutic agent.

As used herein, "non-cytotoxic bioreductive moiety" is used to define any bioreductive moiety having substantially no cytotoxic activity in vivo. Thus, it is intended that the bioreductive moiety for use in accordance with the invention is not only in itself non-cytotoxic, but that this produces substantially no cytotoxic species following bioreductive activation. By "non-cytotoxic" it is meant that the bioreductive moiety does not interact directly with DNA. Preferably, the bioreductive moiety is substantially non-mutagenic. Thus, the bioreductive moiety is intended to function merely as a non-cytotoxic carrier or targeting agent for the drug species which, following delivery of the drug at the target site, is eliminated from the body in the absence of any undesirable side-effects.

The bioreductive conjugates in accordance with the invention have a targeting effect on tissues having reductase activity. This is believed to be a consequence of hypoxic metabolism and/or reduced oxygenation of such tissues.

In one embodiment the invention provides bioreductive conjugates of formula (I):

$A(B)_n$         (I)

where A is a non-cytotoxic bioreductive moiety, each B is independently the residue of a therapeutic agent, and n is an integer, preferably from 1 to 3, particularly 1.

A and B are stably conjugated in an oxygenated environment and are such that A is non-cytotoxic and B when conjugated to A is non-cytotoxic. On reductive activation of A, A and B detach and A is itself either a stable, non-cytotoxic species or, more preferably, A reacts with itself to form a stable, non-cytotoxic species.

Preferred compounds for use in accordance with the invention are those which have the ability to penetrate poorly perfused tissues and which only release the active drug in a hypoxic and/or ischemic environment.

A large number of bioreductive agents of diverse structure are known. These include quinones, aromatic nitro compounds and N-oxides. As mentioned above, those intended for use in accordance with the invention should be substantially non-cytotoxic following bioreductive activation. This may be achieved in a number of ways.

Following bioreduction of the conjugate and delivery of the drug species to the target site, the final form of the bioreductive carrier may itself comprise a stable, non-cytotoxic species, for example a compound having no potential alkylating centre. However, in a preferred embodiment of the invention, cytotoxicity of the bioreductive moiety may be reduced by providing a nucleophilic centre within the bioreductive compound itself. Following release of the drug an alkylating centre is formed. However, the proximity of the nucleophilic centre ensures that intramolecular alkylation occurs in preference to alkylation of any biomolecules such as DNA. In this way, substantially no cytotoxic species are formed. Such systems may be referred to as "self-alkylating".

Examples of electron rich groups capable of acting as a nucleophilic moiety in the bioreductive compound include oxygen, sulphur and nitrogen atoms. Thus, for example, inclusion of a suitably positioned amino, thio or hydroxyl group within the bioreductive compound will favour intramolecular alkylation resulting in a non-cytotoxic product on release of the drug at the site of hypoxia/ischemia. Suitable nucleophilic moieties which may be present in the bioreductive moiety include —OH, —SH, —NH$_2$ and —NHR in which R is $C_{1-6}$ alkyl, e.g. $C_{1-3}$ alkyl. Other suitable nucleophilic moieties will be known to those skilled in the art.

Alternatively, the bioreductive compound for use in the invention may be rendered non-cytotoxic following drug delivery by means of the introduction of steric hindrance capable of presenting a physical blockage to attack upon the bioreductive by any nucleophile. Thus, the presence of a bulky group either at or in close proximity to any potential alkylating centre generated in the bioreductive moiety following drug delivery serves to abolish alkylating reactivity thus preventing alkylation of any biomolecules. Examples of groups which may be used in this way include linear or, more preferably, branched, $C_{4-20}$ alkyl or alkenyl groups, e.g. tert. butyl. Other groups capable of providing steric hindrance will be known to those skilled in the art.

Particularly preferred bioreductive conjugates in accordance with the invention include compounds of formula II:

(wherein $R^1$ and $R^2$ independently represent hydrogen or halogen atoms, or a group R, OR, SR, NHR, NR$_2$, CO$_2$R or CONHR;

or, alternatively, $R^1$ and $R^2$ together with the intervening ring carbon atoms form a 5-7 membered, preferably 5- or 6-membered, carbocyclic or heterocyclic ring itself optionally substituted by one or more halogen atoms, or by one or more groups selected from R, OR, SR, NHR, NR$_2$, CO$_2$R and CONHR;

Z represents an alkyl, alkenyl, aryl or aralkyl group optionally carrying at least one OH, SH, NH$_2$ or NHR$^7$ group in which R$^7$ is an alkyl group;

$R^3$, $R^4$, $R^5$ and $R^6$ independently represent hydrogen atoms or an alkyl or alkenyl group;

each group R independently represents a hydrogen atom, an alkyl or alkenyl group;

E represents the residue of a therapeutic agent to be delivered, optionally attached via a linking group L;

m=0, 1, 2 or 3, preferably 1;

p=0 or 2, preferably 0;

with the proviso that when m=1 then p=0)

or a salt thereof.

Preferred compounds of formula II include those wherein Z represents a group of the formula (CH$_2$)$_n$XH in which n=0, 1, 2 or 3, preferably 0; and X represents an oxygen or sulphur atom or, preferably, X represents a group of formula NY wherein Y represents a hydrogen atom or an alkyl group. Such compounds may act as "self-alkylating" systems.

Particularly preferred compounds of formula II are those wherein Z represents a group of the formula (CH$_2$)$_n$XH in which X represents an amino group;

$R^1$ and $R^2$ each represent alkoxy groups or, together with the intervening ring carbon atoms, $R^1$ and $R^2$ form a benzene ring;

$R^3$, $R^4$, $R^5$ and $R^6$ each represent hydrogen atoms; and n=0, m=1 and p=0.

Alternatively, in relation to the compounds of formula II, particularly when Z is other than a group of the formula $(CH_2)_nXH$, reduction of the quinone to its hydroquinone form may facilitate an intramolecular cyclisation reaction via the hydroxy group present on the hydroquinone ring and subsequent elimination of the drug species. The resulting cyclic ether is non-cytotoxic.

Reaction scheme 1 below illustrates the preparation of a preferred bioreductive conjugate of formula II in which $R^1$, $R^2$ and Z are as hereinbefore defined. As will be seen, bioreductive activation of the conjugate results in the formation of a cyclic ether which is an analogue of vitamin E and non-cytotoxic.

Scheme 1:

Other preferred bioreductive conjugates in accordance with the invention include those compounds of formula III:

(wherein

P and Q together with the intervening ring carbon atoms form a quinone or indoloquinone ring, a nitroaromatic, N-oxide or diazoaromatic compound, itself optionally substituted by one or more halogen atoms, or by one or more groups selected from R, OR, SR, NHR, $NR_2$, $CO_2R$ and CONHR;

$R^1$ represents a hydrogen or halogen atom, or a group R, OR, SR, NHR, $NR_2$, $CO_2R$ or CONHR;

$R^3$, $R^4$ and $R^5$ independently represent hydrogen atoms or an alkyl or alkenyl group;

each group R independently represents a hydrogen atom, an alkyl or alkenyl group;

E represents the residue of a therapeutic agent to be delivered, optionally attached via a linking group L);

or a salt thereof.

Preferred compounds of formula III are those wherein P and Q together with the intervening ring carbon atoms form a quinone or indoloquinone ring; and $R^1$, $R^3$, $R^4$ and $R^5$ each represent hydrogen atoms or methyl groups.

To act as "self-alkylating" systems, the electron-rich heteroatom present in the reduced form of the ring system of the compounds of formula III should preferably be no more than 6 bonds from the carbon atom linked to the therapeutic agent, E.

Other preferred bioreductive conjugates in accordance with the invention include the compounds of formula IV:

(IV)

(wherein

S and T together with the intervening ring carbon atoms form a quinone or iminoquinone ring, a nitroaromatic or N-oxide, e.g. an aromatic N-oxide, compound, itself optionally substituted by one or more halogen atoms, or by one or more groups selected from R, OR, SR, NHR, $NR_2$, $CO_2R$ and CONHR;

Z represents an alkyl, alkenyl, aryl or aralkyl group optionally carrying at least one OH, SH, $NH_2$ or $NHR^6$ group in which $R^6$ is an alkyl group;

$R^7$ represents an alkyl group, preferably $C_{1-2}$ alkyl;

$R^3$, $R^4$ and $R^5$ independently represent hydrogen atoms or an alkyl or alkenyl group;

each group R independently represents a hydrogen atom, an alkyl or alkenyl group;

q=0, 1, 2 or 3, preferably 0 or 1;

E represents the residue of a therapeutic agent to be delivered, optionally attached via a linking group L);

or a salt thereof.

Preferred compounds of formula IV are those in which S and T together with the intervening ring carbon atoms form a quinone or N-oxide compound;

$R^3$, $R^4$ and $R^5$ each represent hydrogen atoms;

$R^7$ is methyl;

Z represents a group of formula $(CH_2)_nXH$ wherein X represents an oxygen or sulphur atom or, preferably, a group of formula NY in which Y represents a hydrogen atom or an alkyl group, and n=0, 1, 2 or 3; and q=0 or 1.

In relation to the compounds of formula IV, alkylating activity may effectively be abolished following drug delivery by choosing as group Z a bulky group capable of providing steric hindrance. In such cases, Z is preferably a linear or, more preferably, branched, $C_{4-20}$ alkyl or alkenyl group. Alternatively, such compounds may act as "self-alkylating" systems in cases where Z represents a group of the formula $(CH_2)_nXH$.

In each of the compounds of general formulae II-IV above, the substituents R, $R^1$, $R^2$, $R^3$, $R^4$, $R^5$, $R^6$ and $R^7$ may be selected to provide the conjugate with optimum redox potential, solubility, enzyme specificity etc.

As used herein, the term "heterocyclic group" is intended to define a carbocyclic group interrupted by at least one heteroatom selected from oxygen, sulphur and nitrogen.

Examples of preferred carbocyclic or heterocyclic rings include benzene, pyridine, pyrrole, furan, pyrazine, piperidine, piperazine, pyrrolidine, morpholine and thiomorpholine rings.

In each of the compounds of formulae II-IV, preferred halogen atoms are fluorine and chlorine.

In the bioreductive conjugates of the invention, any alkyl or alkenyl moiety, unless otherwise stated, may be straight-chained or branched and preferably contains from 1 to 8, more preferably 1 to 6, and especially preferably 1 to 4, carbon atoms. Aryl moieties, unless otherwise stated, preferably contain from 5 to 12 ring atoms and especially preferably comprise phenyl rings.

Preferred salts of the compounds of formulae I-IV are those which are suitable for administration to patients and are thus pharmaceutically or physiologically acceptable salts. Such salts may be formed with various inorganic and organic acids and include the ammonium, alkali and alkaline earth metal salts.

Reductases known to be involved in activation of bioreductive compounds include DT diaphorase, cytochrome P450, NADPH-dependent cytochrome P450 reductase and xanthine oxidase. The ease of reduction of any given bioreductive agent will depend upon its ability to act as a substrate for the intracellular reductases and the expression levels of such enzymes within the particular cell type. The choice of bioreductive compound for use in the invention will thus depend upon the type of enzymes present at the target site. Indeed, it may be useful to determine the relative enzyme activities in the target tissues of individual patients before starting treatment.

It is clearly desirable that the bioreductive conjugate should reach the target site intact. Since bioreduction of the conjugate is dependent upon the redox potential of the bioreductive moiety present, this may be selected such that this is less susceptible to reduction by ubiquitous systems such as NADH or NADPH, thereby increasing the chances that the conjugate will reach the target site still intact. In general, those bioreductive compounds having an optimal redox potential will be more selective in targeting of hypoxic cells and are thus preferred for use in the invention.

Examples of bioreductive compounds preferred for use in the invention include the quinones, naphthoquinones, indoloquinones and quinolino quinones and their derivatives. The electron deficient quinone nucleus in such compounds readily undergoes reduction in vivo to form the corresponding electron rich hydroquinone which in turn is capable of intramolecular rearrangement to release the drug. Particularly preferred quinones include the 1,4-benzoquinones and the naphthoquinones in which the quinone ring carries an optionally hydroxy or amino substituted alkenyl group, e.g. a propenyl group, and an adjacent nucleophilic moiety, e.g. an amino group. Indoloquinones are particularly good substrates for DT diaphorase, an enzyme commonly found in most tissues.

A particularly preferred bioreductive conjugate in accordance with the invention is shown in reaction scheme 2 given below in which the bioreductive moiety is a 1,4-benzoquinone and the therapeutic agent is dexamethasone, an anti-inflammatory agent which may be used in the treatment of rheumatoid arthritis.

Scheme 2:

self-immobilised metabolite

DEXAMETHASONE
20

The invention is considered to have utility in connection with the delivery of a wide range of therapeutic agents. The expressions "therapeutic agent" and "drug" are used interchangeably herein and are intended to define any atom, ion or molecule which in vivo is capable of producing an effect detectable by any chemical, physical or biological examination. A therapeutic agent will in general be any substance which may be administered to a human or non-human animal body to produce a desired, usually beneficial, effect and may be an agent having either a therapeutic or a prophylactic effect.

Examples of therapeutic agents suitable for use in accordance with the invention include agents in all of the major therapeutic areas including anti-infectives such as antibiotics and antiviral agents, analgesics, anaesthetics and anti-inflammatory agents. Anti-neoplastics, including known cytotoxic agents may also be used. The exact choice of therapeutic agent will naturally depend upon the desired therapeutic application.

Whilst it is envisaged that in general the therapeutic agent will itself be non-cytotoxic, the bioreductive carrier may be used to deliver cytotoxic agents, e.g. in anti-tumor treatment.

Examples of other therapeutic agents for use in accordance with the invention include agents administered to the human or animal body for diagnostic purposes, e.g. for use in radio-imaging techniques. In this regard, a radiolabelled steroid may be linked to a non-cytotoxic bioreductive compound for use in the detection of hypoxic cells in tumor tissues.

Methods for attaching bioreductive compounds to a therapeutic agent are within the level of skill in the art. In general, the conjugates in accordance with the invention can be prepared by linkage of a non-cytotoxic bioreductive moiety to at least one therapeutic agent. Linkage of the therapeutic agent to the bioreductive moiety may be effected through any reactive group and standard coupling techniques are known in the art. Preferred reaction conditions, e.g. temperature, solvents, etc. depend primarily on the particular reactants and can readily be determined by those skilled in the art. In general, any reactive groups present, e.g. amino, carboxy etc. will be protected during coupling of the bioreductive with the therapeutic agent, although it is possible to leave some groups unprotected. After coupling, the resulting compound may be purified, e.g. by chromatography.

The bioreductive moiety may be bonded directly to the therapeutic agent or may be bonded by a linker group, L. Linkage between the bioreductive and the therapeutic agent may be effected via any reactive group present in the bioreductive moiety, e.g. a primary amine, carboxylate, alcohol, thiolate, etc. Preferably, the bioreductive moiety is linked to the therapeutic agent via an ester, phosphate ester, ether, amine, thiol or thiol ester bond or any combination thereof.

The linker group serves to link the bioreductive moiety to at least one therapeutic agent. Besides filling this role as a linker, the linker group may be selected to yield a bioreductive conjugate having desired characteristics. For example, appropriate choice of a linker group may serve to enhance the resistance of the conjugate to non-bioreductive metabolism and/or enhance delivery of the drug molecule at the target site. It may also be possible to optimise the redox potential, enzyme or tissue specificity, or the solubility of the conjugate by attaching to or incorporating within the linker group appropriately selected moieties, e.g. groups which are tissue targeting. Thus, the ability to alter the nature of the linker group provides for the possibility of altering the physico-chemical properties, e.g. solubility, and biological properties, e.g. biodistribution, of the bioreductive conjugate. The primary function of the linker is however to link together the bioreductive compound and the drug.

Linker groups L particularly suitable for use in the invention for those drugs having a free —OH or —SH group include the following in which E represents the residue of a drug species:

and (wherein n is an integer from 1 to 3;

X represents a sulphur or oxygen atom which may form part of the drug molecule E;

and $R^8$ and $R^9$ each independently represent F or Cl).

The bioreductive itself may be synthesised in accordance with conventional synthesis techniques. Techniques for the synthesis of quinones, in particular indoloquinones are described for example in J. Org. Chem. 50:4276-4281 (1985).

Viewed from a further aspect the invention provides a process for the preparation of a bioreductive conjugate comprising a non-cytotoxic bioreductive moiety with linked thereto at least one therapeutic agent, said process comprising linking at least one therapeutic agent to a non-cytotoxic bioreductive moiety.

There are believed to be many conditions which may benefit from the drug delivery system of the invention. These are primarily conditions associated with hypoxia and/or ischemia. Hypoxia is any state in which a physiologically inadequate amount of oxygen is available to, or utilised by, any given tissue or group of tissues within the body. Ischemia is any local diminution in the blood supply to any tissue in the body and may arise as a result of obstruction in the flow of arterial blood or vasoconstriction. In general, ischemia will ultimately lead to hypoxia.

In a clinical setting, tissues may become hypoxic and/or ischemic as a result of a number of different conditions in the body. Reduction of the blood supply to body tissues has the effect of inducing ischemia, for example in atherosclerosis, diabetes or following tissue or organ transplantation. Inflammatory or cancerous response may also lead to the tissue either physically or metabolically outgrowing its vascular supply, again leading to ischemia and/or hypoxia.

Non-limiting examples of conditions which may be treated using the bioreductive conjugates of the invention include inflammatory conditions, e.g. rheumatoid arthritis, and other arthritic conditions such as osteoarthritis, diabetes, atherosclerosis, stroke, sepsis, Alzheimer's disease and other neurological diseases, cancer, kidney disease, digestive diseases and liver disease. Other conditions of interest include chronic periodontitis and ischemia following tissue transplantation.

The bioreductive conjugates of the invention may also find use in the treatment of a wide range of inflammatory conditions in which hypoxia and/or ischemia may be implicated, in particular in treating inflammatory conditions of the soft tissues. In the case of certain inflammatory conditions of the gastrointestinal tract, sections of the g.i. tract become hypoxic. Other inflammatory conditions which may be treated in accordance with the invention thus include gastrointestinal disorders such as Crohn's disease.

The compounds of the invention may also be used in the treatment of muscular disorders associated with hypoxia and/or ischemia.

It is believed that many known drugs could have enhanced therapeutic effects if selectively delivered to ischemic/hypoxic tissue. For example, following a cerebral attack, cerebral perfusion is reduced and the brain suffers an inflammatory response. The linkage of a vasodilator, such as a nitric oxide generator, or an anti-inflammatory agent, such as a steroid, to a bioreductive agent would thus serve to enhance the therapeutic index of the drug.

Rheumatoid arthritis is known to be associated with chronic synovial inflammation and poor perfusion of the synovial tissues. However, we have now discovered that in patients suffering from rheumatoid arthritis the synovial tissues are in many cases profoundly hypoxic ($pO_2$<12 mm Hg). We have also found that such tissues contain high levels of reductases. Whilst not wishing to be bound by theoretical considerations, it is believed that there are pockets in the synovium which are hypoxic and that it is the hypoxic cells in the synovium which are primarily responsible for the inflammation associated with rheumatoid arthritis. Linkage of an anti-inflammatory agent, such as a non-steroidal anti-inflammatory agent, e.g. dexamethasone, a steroid or a nitric oxide inhibitor would thus serve to greatly increase the therapeutic index of the active agent in the treatment of rheumatoid arthritis, whilst at the same time reducing the risk of systemic side effects. The weak acidic based NSAIDs which undergo ion-trapping in acidic tissue are considered particularly suitable.

Following transplantation and tissue rejection, both ischemia and an immunological-inflammatory response may contribute to tissue hypoxia. Again, such conditions may thus be treated using a conjugate of the invention in which a bioreductive moiety is linked to a vasodilator or to an anti-inflammatory or immunological suppressant.

Many of the basic complications of diabetes are believed to owe their basic pathology to hypoxia. Indeed, in many cases diabetics show accelerated atherosclerosis. The present invention may thus be used in the treatment of diabetes by linking a drug, such as a phosphodiesterase inhibitor, to a non-cytotoxic bioreductive moiety.

Hypoxic tissues are also believed to be present in chronic periodontitis, a condition associated with severe inflammation of the periodontium. Linkage of an antibiotic or other drug known for treating periodontitis, e.g. a metalloproteinase inhibitor, to a bioreductive may thus be beneficial in treating this condition.

An example of an agent which may be linked to a non-cytotoxic bioreductive compound for use in treating diabetes is dipyridamole.

Viewed from a yet further aspect, the invention provides a bioreductive conjugate as hereinbefore defined for use in a method of targeting a therapeutic agent to a specific tissue site within the body, in particular to a site of hypoxia and/or ischemia, e.g. in the treatment of rheumatoid arthritis or other arthritic conditions, diabetes, atherosclerosis, stroke, sepsis, Alzheimer's disease and other neurological disorders, cancer, kidney disease, digestive diseases, liver disease, chronic periodontitis or ischemia following tissue transplantation.

In a preferred embodiment the invention provides a bioreductive conjugate comprising a non-cytotoxic bioreductive moiety linked to an anti-inflammatory agent for use in the treatment of rheumatoid arthritis.

Viewed from a yet further aspect the invention provides the use of a bioreductive conjugate as hereinbefore defined in the manufacture of a medicament for use as a targeting agent, in particular as an agent capable of targeting a site of hypoxia and/or ischemia within the body, e.g. in the treatment of rheumatoid arthritis and other arthritic conditions, diabetes, atherosclerosis, stroke, sepsis, Alzheimer's disease and other neurological disorders, cancer, kidney disease, digestive diseases, liver disease, chronic periodontitis or ischemia following tissue transplantation.

In another aspect the invention provides a method of targeting hypoxic and/or ischemic tissues in the human or non-human, preferably mammalian, body comprising administering to said body a bioreductive conjugate as hereinbefore defined. In particular, the invention provides a method of treating or preventing rheumatoid arthritis and other arthritic conditions, diabetes, atherosclerosis, stroke, sepsis, Alzheimer's disease and other neurological disorders, cancer, kidney disease, digestive diseases, liver disease, chronic periodontitis or ischemia following tissue transplantation, said method comprising administering to a human or non-human animal body in need thereof an effective amount of a bioreductive conjugate as hereinbefore defined.

Viewed from a yet further aspect the invention provides a pharmaceutical composition comprising a bioreductive conjugate in accordance with the invention or a pharmaceutically acceptable salt thereof, together with at least one pharmaceutical carrier or excipient.

The active ingredient in such compositions may comprise from about 0.1% to about 99% by weight of the formulation. By "pharmaceutically acceptable" is meant that the ingredient must be compatible with other ingredients of the compositions as well as physiologically acceptable to the patient.

Pharmaceutical compositions for use according to the present invention may be formulated in conventional manner using readily available pharmaceutical or veterinary aids. Thus the active ingredient may be incorporated, optionally together with other active substances, with one or more conventional carriers, diluents and/or excipients, to produce conventional galenic preparations such as tablets, pills, powders, lozenges, sachets, cachets, elixirs, suspensions, emulsions, solutions, syrups, aerosols, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents, sweetening agents, flavouring agents, and the like. The formulations may be formulated so as to provide quick, sustained or delayed release of the active ingredient after administration to the patient by use of procedures well known in the art.

The compositions are preferably formulated in a unit dosage form, e.g. with each dosage containing from about 0.1 to about 500 mg of the active ingredient.

The precise dosage of the active ingredient and the length of the treatment will depend upon a number of factors including the age and weight of the patient, the specific condition being treated and its severity, and the route of administration. In general, an effective dose will be of the order of from about 0.01 mg/kg to about 20 mg/kg bodyweight per day, e.g. from about 0.05 to about 10 mg/kg per day, administered one or more times daily. Thus, an appropriate dose for an adult may be from 10 to 100 mg per day, e.g. 20 to 50 mg per day.

Administration may be by any suitable method known in the art, including for example oral, parenteral (e.g. intramuscular, subcutaneous, intraperitoneal or intravenous), rectal or topical administration.

The present invention will now be further illustrated by way of the following non-limiting Examples and with reference to accompanying FIG. 1 which shows the product profile obtained on the reduction of the aspirin-bioreductive conjugate of Example 5 by the $(CH_3)_2C.OH$ radical.

EXAMPLE 1

Synthesis of "Self-Alkylating" Bioreductive Delivery System (5)

(6)

Step 1—N,N-dimethyl formamide (2 equivs) and POCl₃ are stirred together. The resulting solution is then added to a solution of the protected amino-dihydro-napthoquinone (1 equiv) in 1,2-dichloroethane and heated under reflux for about 1½ hours. The resulting solution is then cooled and NaOAc (1M, 100 mL/g quinone) is added with stirring over 2% hours. The solution is then extracted with EtOAc, dried and evaporated. The resulting product (2) is then purified by chromatography on silica.

Step 2—triethylphosphonoacetate (10.92 mmol) is stirred into dimethylformamide (80 ml). NaOMe (11 mmol) is then added and the solution is stirred for ½ hour. Product (2) (4.27 mmol) dissolved in dimethylformamide (20 ml) is added stepwise and stirring is continued for a further 2 hours. The mixture is then diluted with ethyl acetate (300 mL), washed with aqueous sodium hydrogen carbonate (6×100 mL), dried, evaporated in vacuo and the product (3) is recrystallised from ethyl acetate.

Step 3—Product (3) (1.21 mmol) is dissolved in anhydrous CH₂Cl₂ (90 mL) and diisobutylaluminum hydride (16.3 mL, 1.5M in toluene) is added dropwise at –50° C. The mixture is then stirred for 3½ hours at –30° C. and FeCl₃ (1.0M dissolved in 0.1M HCl, 27 mL) is added keeping the temperature below 0° C. Stirring is continued for a further ½ hour at 0° C. followed by filtration. The resulting product is extracted with CHCl₃ (4×75 mL), washed with brine (50 mL), dried and evaporated in vacuo. Product (4) is recrystallised in ethanol.

Step 4—prednisolene 21-acetate (1 equiv) is dissolved in dry CH₂Cl₂ (50 mL) and dry pyridine (10 mL) is added under an atmosphere of nitrogen. The solution is then stirred under reflux for 2 hours together with succinyl chloride (1.1 equivs). This is then cooled and washed with dilute HCl (0.1M, 20 mL) followed by H₂O (3×30 mL), dried and evaporated in vacuo. Product (5) is purified by chromatography on silica.

Step 5—pyridine (6 mmol), N,N'-dimethylphosphoramidic dichloride (3 mmol) and product (4) (4 mmol) are added to a solution of product (5) (2 mmol) in 1,2-dimethoxyethane (10 mL) at 0° C. The resulting solution is stirred at ambient temperature under an atmosphere of argon for 16 hours. This is then poured into ice cold 1N HCl (40 mL) and extracted with CH₂Cl₂ (4×30 mL). The combined extracts are dried with MgSO₄, filtered and concentrated. The residue is purified by column chromatography on silica gel to give the final product (6).

EXAMPLE 2

Synthesis of "Self-Alkylating" Bioreductive Delivery System

-continued

Step 1—Compound (1) (10 mmol) (see Naylor et al., 2-Cyclopropyl Indoloquinones and their Analogues As Bioreductively-Activated Antitumor Agents: Structure-Activity in vitro and Efficacy in vivo, J. Med. Chem.: 40(15), 1997) is dissolved in DMF (10 mL) and methyl 3-aminocrotonate (50 mmol) is added. The reaction mixture is stirred at ambient temperature for 18 hours and then evaporated in vacuo and the residue purified on silica to give product (2).

Step 2—the aminocrotonate derivative (2) (10 mmol) is dissolved in $CHCl_3$ (300 mL) and EtOH (110 mL) and a solution of $Na_2S_2O_4$ (120 mmol) in $H_2O$ (130 mL) added. The solution is stirred at ambient temperature for ½ hour and the organic layer separated, washed with saturated NaCl (500 mL), dried and evaporated. The crude hydroquinone is then dissolved in anhydrous $CH_2Cl_2$ (300 mL) under argon, cooled to −30° C. and DIBAL-H (50 mL of a 1.5M solution in toluene) added dropwise such that the solution temperature remains below −30° C. The solution is then allowed to reach 0° C. and stirred for 2½ hours at this temperature, and a solution of solution of $FeCl_3$ (90 mL, 1.0M (0.1M HCl)) added. The solution is stirred for 10 min at 0° C. and then $CHCl_3$ (500 mL) and $H_2O$ (500 mL) added. The aqueous layer is extracted with $CHCl_3$ (5×250 mL) then EtOAc (5×250 mL) and the combined organic phases washed with saturated NaCl (500 mL), dried and evaporated. The residue is purified on silica and recrystallized from EtOAc to give product (3) as a purple/red solid.

Step 3—the indoloquinone (3) (10 mmol) is dissolved in THF (25 mL) and added to a solution (THF, 25 mL) of the drug carboxylic acid or phenol to be coupled (1.5 equivs), triphenylphosphine (20 mmol) and diethylazodicarboxylate (20 mmol). The solution is then stirred overnight at 50° C., the solvent evaporated and the residual final product (4) is purified on silica.

EXAMPLE 3

Synthesis of "Self-Alkylating" Bioreductive Delivery System

-continued

Step 1—Methyl 5-Methoxy-1-methylindole-2-acetate (10 mmol) is dissolved in anhydrous THF (250 mL) and LiAlH$_4$ (100 mL of a 1.0M solution in THF) added dropwise at ambient temperature and under argon. The solution is then stirred for 1 hour at 30° C. and then EtOAc (250 mL) added, followed by the gradual addition of H$_2$O (150 mL). The solution is washed with HCl (0.1M, 250 mL) and saturated NaCl (250 mL), dried and evaporated. The residue is purified by flash column chromatography on silica and then recrystallized to give product (2).

Step 2—DMF (100 mmol) and POCl$_3$ (25 mmol) are stirred at −5° C. for ¾ hour and then a solution of (2) (10 mmol in 30 mL DMF) is added slowly, maintaining the temperature at about 0° C., and then warmed to 40° C. and stirred for 1 hour. Ice/water (100 mL) is then added, followed by NaOH (37%, 50 mL) and the solution extracted into EtOAc, evaporated and the carboxaldehyde (3) purified by recrystallization from an EtOAc/hexane mixture.

Step 3—to a solution of (3) (10 mmol) in AcOH (50 mL) cooled to 5° C., is added dropwise a cold (0° C.) mixture of fuming HNO$_3$ (10 mL) in AcOH (30 mL). The solution is stirred for 1 hour while allowing to reach ambient temperature, and then poured onto 100 g of crushed ice. After 15 minutes stirring the resulting yellow solid is collected by suction filtration. The dried residue is purified on silica to give product (4) as a yellow solid.

Step 4—to a suspension of (4) (10 mmol) in EtOH (180 mL) is added tin powder (40 mmol) and HCl (3.0M, 70 mL) and the solution stirred at ambient temperature for 1 hour. The solution is then decanted from the excess tin and neutralized with saturated NaHCO$_3$ (aq.). The resulting suspension is then added to an equal volume of H₂O and extracted with CHCl₃ (5×50 mL) and then EtOAc (5×50 mL) and the combined extracts evaporated. The residual 4-aminoindole derivative is purified on silica and used immediately in the next step by dissolving in Me₂CO (250 mL) and adding a solution of potassium nitrosodisulfonate (($KSO_3)_2NO$, Fremy's salt, 30 mmol)) in $NaH_2PO_4/Na_2HPO_4$ buffer (250 mL, 0.3M, pH 6.0) and the solution stirred at ambient temperature for 1 hour. The Me₂CO is removed in vacuo and the resulting orange precipitate collected by suction filtration, washed with H₂O and dried in a vacuum oven at 45° C. to afford product (5) as an orange solid which is recrystallized from EtOAc.

Step 5—indoloquinone (5) (10 mmol) is dissolved in THF (100 mL) together with Et₃N (10 mmol) and trimethylchlorosilane (1.1 mmol) added. The solution is stirred at ambient temperature for 8 hours, evaporated and purified on silica to give product (6).

Step 6—the protected indoloquinone (6) (10 mmol) is dissolved in anhydrous nitrogen degassed MeOH (200 mL) and NaBH₄ (30 mmol) added. The solution is degassed with argon and stirred for 5 min under argon and then aerated and diluted with EtOAc (700 mL) and washed with H₂O (2×250 mL) and then saturated NaCl (100 mL). The dried organic solution is condensed to give the indoloquinone (7) as an orange solid after silica column and/or recrystallization from EtOAc.

Step 7—the 3-(hydroxymethyl)indoloquinone (7) is dissolved in THF (50 mL) together with triphenylphosphine (20 mmol) and diethylazodicarboxylate (20 mmol) and the desired drug carboxylic acid or phenol (RCO₂H or ROH where R is a drug species, 1.5 to 5 equivs) added. The solution is then stirred overnight at 50° C., the solvent evaporated and the residue redissolved in EtOAc. The solution is then washed with HCl (1.0M, 50 mL) and H₂O (50 mL), dried and evaporated. The product is purified on silica and deprotected by dissolving in anhydrous MeOH together with K₂CO₃ (10 mmol) at 0° C. and stirring for 45 min. The final product (8) is then purified on silica and recrystallized from EtOAc.

EXAMPLE 4

Synthesis of "Self-Alkylating" Bioreductive Delivery System

-continued

"SELF ALKYLATING" VERSION

Step 1—7-Azaindole (Sigma-Aldrich, 10 mmol) is added gradually with stirring to a suspension of NaH (11 mmol) in THF (30 mL). After 15 minutes, methyl iodide (10 mmol) is added and the solution stirred at ambient temperature for 1 hour. The solution is cooled to −5° C. and $H_2O$ (30 mL) added gradually, followed by EtOAc (50 mL). The aqueous layer is then further extracted with EtOAc (3×50 mL), washed with saturated $NaHCO_3$, saturated NaCl, dried and evaporated. The residue is purified on silica to give product (2).

Step 2—DMF (100 mmol) and $POCl_3$ (25 mmol) are stirred at −5° C. for ½ hour and then a solution of (2) (10 mmol in 30 mL DMF) is added slowly, maintaining the temperature at about 0° C., and then warmed to 40° C. and stirred for 1 hour. Ice/water (100 mL) is then added, followed by NaOH (37%, 50 mL) and the solution extracted into EtOAc, evaporated and the carboxaldehyde (3) purified by recrystallization from an EtOAc/hexane mixture.

Step 3—the 3-formyl-7-azaindole (3) (10 mmol) is dissolved in anhydrous nitrogen degassed MeOH (200 mL) and $NaBH_4$ (30 mmol) added. The solution is degassed with argon and stirred for 5 min under argon and then aerated and diluted with EtOAc (700 mL) and washed with $H_2O$ (2×250 mL) and then saturated NaCl (100 mL). The dried organic solution is condensed to give the 3-hydroxymethyl derivative (4) after silica column chromatography.

Step 4—product (4) (10 mmol) is dissolved in KOH (0.5M, aq., 100 mL). Caro's acid (potassium peroxymonosulphate, Oxone, $2 KHSO_5.KHSO_4.K_2SO_4$, 10 mmol) is added slowly with stirring and the solution stirred for 12 hours. The solution is neutralised with phosphoric acid, evaporated and the residual salt extracted and purified on silica to afford (5).

Step 5—the 3-(hydroxymethyl)indole (5) (10 mmol) is dissolved in THF (50 mL) together with pyridine (5 mL) and succinylchloride (10 mmol) added with stirring. After 1 hour $H_2O$ (50 mL) is added and the solution stirred for 1½ hours and 2.0M HCl (50 mL) added. After a further 1½ hours the solution is extracted with $Et_2O$ (3×100 mL), dried and evaporated. The acid (6) is purified on silica.

Step 6—the azaindole-N-oxide carboxylic acid (6) (10 mmol) is dissolved in THF (25 mL) and added to a solution (THF, 25 mL) of the protected steroid (1.5 equivs), triphenylphosphine (20 mmol) and diethylazodicarboxylate (20 mmol). The solution is then stirred overnight at 50° C., the solvent evaporated and the residue redissolved in EtOAc. The solution is washed with HCl (1.0M, 50 mL) and saturated $NaHCO_3$ (aq., 50 mL), dried and evaporated. The final product (7) is purified on silica.

EXAMPLE 5

Preparation of 3-(2-Acetoxybenzoyloxy)methyl-1,2-dimethyl-5-methoxyindole-4,7-dione: Aspirin-Bioreductive Conjugate 3-Hydroxymethyl-5-methoxy-1,2-dimethylindole-4,7-dione (0.235 g, 1.0 mmol) was dissolved in dichloromethane (anhydrous, 25 mL) together with pyridine (2.5 mL). 2-Acetylsalicyloyl chloride (0.237 g, 1.2 mmol) was then added and the solution heated under reflux for 1¾ hours, cooled and ethyl acetate (100 mL) added. The solution was washed with HCl (0.1 M, 100 mL) and then saturated NaCl (100 mL), dried and evaporated. The residue was purified on silica gel, eluting with ethyl acetate to afford the title compound as a yellow solid (275 mg, yield: 69.3%) which was recrystallised from ethyl acetate, mp 159-161° C.

$^1$H-NMR ($CDCl_3$) δ 2.27 (s, 3H), 2.31 (s, 3H), 3.81 (s, 3H), 3.90 (s, 3H), 5.47 (s, 2H), 5.63 (s, 1H), 7.01-7.53 (m, 3H) and 7.99 (dd, J=1.4 and 8.1 Hz, 1H) ppm.

Analysis: Found: C, 63.81; H, 4.81; N, 3.71.
Calculated: C, 63.47; H, 4.82; N, 3.52%.

EXAMPLE 6

Pharmacokinetics of the indoloquinone-acetyl salicylic acid conjugate of Example 5 were studied as follows:

Protocol:

Three groups of male Wistar albino rats (n=5) received sterile air dorsally (day 1). After two days a further 20 ml sterile air were administered. On day 5, 2 ml of a 1% carrageenin in sterile saline was injected directly into the air pouch. Animals were housed in metabolic cages.

100 mg of the indoloquinone-aspirin conjugate of Example 5 were suspended in ethanol (2 ml). 50 mg acetyl salicylic acid was dissolved in 2 ml ethanol. 2 ml ethanol was used as a control. 18 ml sterile water were added to each sample.

On day 9, each animal was injected with 4 ml of solution as follows:

Group A—20 mg indoloquinone-aspirin conjugate Group B—10 mg acetyl salicylic acid Group C—ethanol (control)

The animals were then returned to their cages for periods of either 2 (nos. 1, 2 and 3 from each group) or 4 hours (nos. 4 and 5 from each group). After this time the animals were anaesthetized and blood and exudate collected. Available urine was also collected.

Results:

Analysis of the collected samples by HPLC showed that the bioreductive-acetyl salicylic acid conjugate had been cleaved to liberate acetyl salicylic acid.

EXAMPLE 7

The reduction initiated release of aspirin from the indoloquinone-acetyl salicylic acid conjugate of Example 5 was investigated by product analysis (HPLC) following γ-radiolysis of $N_2O$-saturated solutions containing the quinone (100 μM) and 2-propanol (8.3M, 50%, v/v) at pH 7.4.

Figure 1:
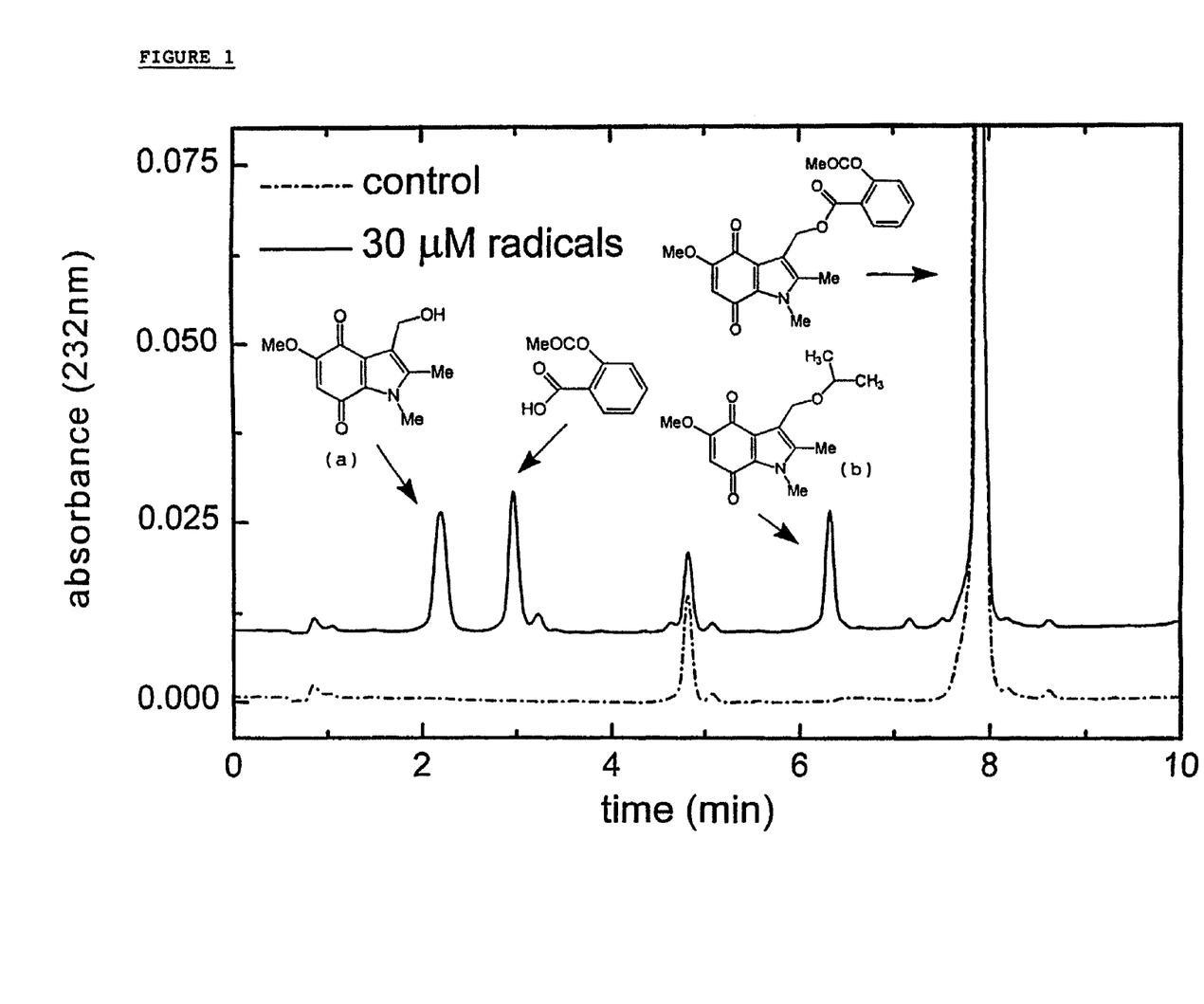

The radiation chemical yield (G) of the $(CH_3)_2C.OH$ radical in $N_2O$-saturated 2-propanol/water mixtures was determined by ferricyanide reduction to be $G((CH_3)_2C.OH)$ =0.67±0.02 μmol $J^{-1}$ in 2-propanol/water (50%, v/v) and 0.72±0.03 μmol $J^{-1}$ in 1 M 2-propanol respectively. FIG. 1 shows the product profile obtained on the reduction of the quinone by the $(CH_3)_2C.OH$ radical. Loss of the parent quinone (G(-Q)=1.63±0.01 μmol $J^{-1}$) parallel the formation of the aspirin leaving group (LG) with G(LG)=1.40±0.15 μmol $J^{-1}$.

The two remaining major peaks in FIG. 1 were derived from the reaction of the resultant iminium derivative with water to generate (a) and with the 2-propanol to generate the isopropyl ether (b). Both of these quinones are generated by autoxidation of their respective hydroquinones following the unavoidable introduction of oxygen during HPLC sampling:

As expected, the relative yields of (a) and (b) were dependent on the alcohol concentration, with the alkylation product virtually disappearing when radiolysis was performed in 1M 2-propanol.

Steady-State γ-Radiolysis

Indolequinone solutions were saturated with $N_2O$ gas in gas-tight vials before irradiation in a $^{60}$Co source. An absorbed dose of 1 Gy=0.67 μM $(CH_3)_2C.OH$ radicals in $N_2O$-saturated 2-propanol/water (50%, v/v). A dose rate of 6-6.5 Gy $min^{-1}$ was used, as determined by Fricke dosimetry and radiation chemical yields were corrected for the absorbed dose in the various alcohol-water mixtures employed.

High Performance Liquid Chromatography (HPLC)

Product analysis following γ-radiolysis was performed by gradient HPLC separation on a 100 mm×4.6 mm base-deactivated reverse-phase column (Hichrom RPB, Hichrom, Reading, U.K.). The eluents were (A): $KH_2PO_4$ (5 mM), $H_3PO_4$ (5 mM), (B): $CH_3CN/H_2O$ (3:1, v/v), with a flow rate of 2 $cm^3$ $min^{-1}$. One of two linear gradients was used for each compound: (1) 35-80% B in 8 min, or (2) 20-50% B in 5 min. Detection was at 232 nm using a Waters 486 detector (Watford, U.K.) and concentrations were determined from peak areas using Waters Maxima software.

EXAMPLE 8

Formulation

A composition suitable for use in the treatment of rheumatoid arthritis is produced using the following ingredients:

| | |
|---|---|
| dexamethasone | 5 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| total | 95 mg |

The active ingredient, starch and cellulose are sieved and mixed thoroughly. The aqueous solution containing polyvinylpyrrolidone is mixed with the resulting powder and the mixture is then passed through a sieve. The resulting granules are dried and sieved again. The sodium carboxymethyl starch, magnesium stearate and talc are sieved and then added to the granules which, after mixing, are compressed on a tablet machine to yield tablets weighing 95 mg.

One tablet taken daily is Suitable for the treatment of patients suffering from rheumatoid arthritis.

The invention claimed is:

1. A bioreductive conjugate of the formula II:

(wherein $R^1$ and $R^2$ independently represent hydrogen or halogen atoms, or a group R, OR, SR, NHR, $NR_2$, $CO_2R$ or CONHR;

or, alternatively, $R^1$ and $R^2$ together with the intervening ring carbon atoms form a 5-7 membered carbocyclic or heterocyclic ring itself optionally substituted by one or more halogen atoms, or by one or more groups selected from R, OR, SR, NHR, $NR_2$, $CO_2R$ and CONHR;

Z represents an alkyl, alkenyl, aryl or aralkyl group optionally carrying at least one OH, SH, $NH_2$ or $NHR^7$ group in which $R^7$ is an alkyl group or Z represents a group of the formula —XH where X represents an oxygen or a sulphur atom, or a group of formula NY in which Y represents a hydrogen atom or an alkyl group;

$R^3$, $R^4$, $R^5$ and $R^6$ independently represent hydrogen atoms or an alkyl or alkenyl group;

each group R independently represents a hydrogen atom, an alkyl or alkenyl group;

E represents the residue of a therapeutic agent to be delivered, optionally attached via a linking group L which is an ester, phosphate ester, ether, amine, thiol or thiol ester group or any combination thereof;

m=0, 1, 2 or 3; and p=0 or 2;

with the proviso that when m=1 then p=0)

or a salt thereof.

2. A bioreductive conjugate as claimed in claim 1, wherein in formula II:

Z represents a group of the formula $(CH_2)_nXH$;

n=1, 2 or 3;

X represents an oxygen or sulphur atom, or a group of formula NY in which Y represents a hydrogen atom or an alkyl group;

or a salt thereof.

3. A bioreductive conjugate as claimed in claim 1, wherein in formula II:

Z represents a group of the formula XH in which X represents an amino group;

$R^1$ and $R^2$ each represent alkoxy groups or, together with the intervening ring carbon atoms, $R^1$ and $R^2$ form a benzene ring;

$R^3$, $R^4$, $R^5$ and $R^6$ each represent hydrogen atoms; and m=1 and p=0;

or a salt thereof.

4. A bioreductive conjugate as claimed in claim 1 wherein said linker group L if present is a group of the formula:

or (wherein n is an integer from 1 to 3;

X represents a sulphur or oxygen atom; and $R^8$ and $R^9$ each independently represent F or Cl).

5. A pharmaceutical composition comprising a bioreductive conjugate as claimed in claim 1, or a pharmaceutically acceptable salt thereof, together with at least one pharmaceutical carrier or excipient.

6. A bioreductive conjugate as claimed in claim 1 for use in a method of targeting a therapeutic agent to a site of hypoxia and/or ischemia within the human or non-human animal body.

7. A method of treating-rheumatoid arthritis or other arthritic conditions, diabetes, atherosclerosis, stroke, sepsis, Alzheimer's disease and other neurological disorders, cancer, kidney disease, digestive diseases, liver disease, chronic periodontitis or ischemia following tissue transplantation comprising administering to a patient in need thereof an amount of the bioreductive conjugate as claimed in claim 1 sufficient to effect said treatment.

8. A method of targeting hypoxic and/or ischemic tissues in the human or non-human animal body, said method comprising administering to said body a bioreductive conjugate as claimed in claim 1.

\* \* \* \* \*